United States Patent
Leighton et al.

(10) Patent No.: US 7,972,589 B2
(45) Date of Patent: Jul. 5, 2011

(54) HAIR FIXATIVE FILM

(75) Inventors: John C. Leighton, Flanders, NJ (US); Michael T. Philbin, Hopewell, NJ (US)

(73) Assignee: Akzo Nobel N.V., Arnhem (NL)

(*) Notice: Subject to any disclaimer, the term of this patent is extended or adjusted under 35 U.S.C. 154(b) by 744 days.

(21) Appl. No.: 10/847,081

(22) Filed: May 17, 2004

(65) Prior Publication Data

US 2005/0255067 A1    Nov. 17, 2005

(51) Int. Cl.
- *A61K 8/02* (2006.01)
- *A61K 8/18* (2006.01)
- *A61Q 5/00* (2006.01)
- *A61Q 5/06* (2006.01)

(52) U.S. Cl. ............ 424/70.11; 424/400; 424/484; 424/486; 424/487; 424/70.1

(58) Field of Classification Search ............ None
See application file for complete search history.

(56) References Cited

U.S. PATENT DOCUMENTS

| | | | |
|---|---|---|---|
| 3,914,403 A * | 10/1975 | Valan ............ | 424/47 |
| 3,975,350 A * | 8/1976 | Hudgin et al. ........ | 524/108 |
| 3,987,162 A * | 10/1976 | Scheuermann ........ | 424/70.17 |
| 3,998,973 A * | 12/1976 | Carlson ............ | 514/770 |
| 4,039,501 A * | 8/1977 | Babcock et al. ........ | 524/107 |
| 4,465,702 A | 8/1984 | Eastman et al. | |
| 4,477,480 A | 10/1984 | Seidel et al. | |
| 4,719,104 A * | 1/1988 | Patel ............ | 424/70.17 |
| 4,849,246 A | 7/1989 | Schmidt | |
| 4,874,604 A | 10/1989 | Sramek | |
| 4,913,897 A | 4/1990 | Chvapil et al. | |
| 5,000,948 A * | 3/1991 | Nandagiri et al. ........ | 424/70.5 |
| 5,037,929 A | 8/1991 | Rajagopalan et al. | |
| 5,131,953 A | 7/1992 | Kasica et al. | |
| 5,149,799 A | 9/1992 | Rubens | |
| 5,187,272 A | 2/1993 | Katcher et al. | |
| 5,266,303 A * | 11/1993 | Myers et al. ........ | 424/47 |
| 5,593,503 A | 1/1997 | Shi et al. | |
| 5,620,683 A * | 4/1997 | Tong et al. ........ | 424/70.11 |
| 5,629,003 A | 5/1997 | Horstmann et al. | |
| 5,766,615 A * | 6/1998 | Narayanan ........ | 424/405 |
| 5,843,881 A * | 12/1998 | Dubois et al. ........ | 512/1 |
| 6,153,222 A | 11/2000 | Becher | |
| 6,177,096 B1 | 1/2001 | Zerbe et al. | |
| 6,197,288 B1 | 3/2001 | Mankoo | |
| 6,586,378 B2 | 7/2003 | Chandra | |
| 6,821,590 B2 * | 11/2004 | Verrall et al. ........ | 428/35.7 |
| 2002/0041857 A1 | 4/2002 | De La Poterie et al. | |
| 2002/0044917 A1 | 4/2002 | De La Poterie et al. | |
| 2002/0051759 A1 | 5/2002 | De La Poterie et al. | |
| 2002/0090348 A1 | 7/2002 | Khoshdel | |
| 2002/0127254 A1 | 9/2002 | Fotinos et al. | |
| 2002/0161088 A1 | 10/2002 | Kochvar et al. | |
| 2003/0017127 A9 | 1/2003 | De La Poterie | |
| 2003/0031640 A9 | 2/2003 | De La Poterie et al. | |
| 2003/0049306 A1 | 5/2003 | Hamamoto et al. | |
| 2003/0099692 A1 * | 5/2003 | Lydzinski et al. ........ | 424/443 |
| 2003/0108505 A1 | 6/2003 | Cao et al. | |
| 2004/0071755 A1 | 4/2004 | Fox | |

FOREIGN PATENT DOCUMENTS

| | | |
|---|---|---|
| CN | 1434696 A | 8/2003 |
| EP | 0 554 818 A1 | 8/1993 |
| EP | 0 937 451 | 8/1999 |
| EP | 1002530 A2 | 5/2000 |
| EP | 275368 A1 | 1/2003 |
| EP | 00750905 A2 | 1/2003 |
| JP | 6126323 * | 12/1986 |
| JP | 6126323 A * | 12/1986 |
| JP | 61286323 * | 12/1986 |
| JP | 11311109 A2 | 5/1989 |
| JP | 2001 294517 | 10/2001 |
| JP | 2002 187824 | 7/2002 |
| JP | P2002212027 A | 7/2002 |
| JP | 2002 528475 | 9/2002 |
| JP | 2003 213038 | 7/2003 |
| WO | WO 95/04082 | 2/1995 |
| WO | WO 01/23460 A1 | 4/2001 |
| WO | WO 01/87244 A1 | 11/2001 |
| WO | WO 02/05789 A2 | 1/2002 |
| WO | WO 02/060397 | 8/2002 |
| WO | WO 03/030881 A1 | 4/2003 |
| WO | WO 03/030882 A1 | 4/2003 |
| WO | WO03/031637 A1 | 4/2003 |
| WO | WO 03/075812 | 9/2003 |
| WO | WO 03/075812 A1 * | 9/2003 |
| WO | WO 03/096996 | 11/2003 |
| WO | WO 2004/037217 | 5/2004 |

OTHER PUBLICATIONS

O.B. Wurzburg, M.S., Modified Starches: Properties and Uses, CRC Press, Inc., Boca Raton, Florida (1986).
Whistler et al., Starch: Chemistry and Technology "Production of Use of Pregelatinized Starch", vol. III, Chapter XXII, pp. 523-536 (1967).
English Translation of "Technology of Cosmetics", Lili et al., 2nd Edition, Chinese Light Industry Publishing House (May 1999).
Chinese Office Action mailed Oct. 12, 2007.

* cited by examiner

*Primary Examiner* — Anand Desai
*Assistant Examiner* — Melissa Mercier
(74) *Attorney, Agent, or Firm* — Norris McLaughlin & Marcus, P.A.

(57) ABSTRACT

The present invention relates to a hair fixative film, which contains a natural and/or synthetic polymer as the main component and a method of applying said film to hair. Such film is useful in maintaining a desired look and style of hair. Furthermore, the film is beneficial because it enables the combination of ingredients that are incompatible in other application forms.

14 Claims, No Drawings

HAIR FIXATIVE FILM

BACKGROUND OF THE INVENTION

The present invention relates to a hair fixative film composition, and methods of fixing and maintaining the hair in a given style by applying said hair fixative film composition to the hair shafts.

A significant portion of the globe uses some sort of hair styling product as part of a grooming routine. These styling products come in a variety of forms. These forms include non-aerosol and aerosol hair sprays, aerosol and non-aerosol mousses, gels, glazes, styling waters, spray gels, spray mousses, waxes, pastes, pomades, and ringing gels, among others. The overall market for these hair styling products continues to grow even though some specific categories have been flat or declining in recent years. There are many reasons for the market decline of some application types, but one reason is that each application has some inherent limitations. These limitations can create performance and aesthetic weaknesses.

Ingredient incompatibility is one such limitation. For instance, incompatibilities between traditional gel thickening polymers and traditional high performance styling polymers lead to less than ideal product properties. These traditional high performance polymers provide superior humidity resistance and setting power to common polymers compatible in gels, but the combination with popular thickeners such as carbomer, a cross-linked polyacrylate, results in hazy gels with poor rheology.

Additional application type limitations include the inability to include polymers with poor solution stability, limits on polymer use levels, product bulkiness, and inconvenience of use. Therefore, there exists a need for new application methods that deliver excellent hair fixative properties, have no negative ecological perceptions, provide formulation versatility, and are fun and convenient to use.

Recently, a new composition for delivering hair fixative polymers from a starch film has been disclosed in U.S. patent application 2003/0099692. Surprisingly, it has now been found that with proper formulation traditional high performance hair fixative polymers can be formed into acceptable films, which can be used as hair fixative films, without the addition of starch or any other film forming polymer as the delivery vehicle. It has also surprisingly been found that films containing hair fixative polymers can also be created containing starch and large amounts of plasticizer. Such films may provide such benefits as excellent high humidity curl retention, film toughness, gloss, stiffness, combing ease, static properties, spring, and webbing when applied to hair. In addition, such films may be more efficient as the hair fixative polymer is less diluted by the addition of other non-functional ingredients.

SUMMARY OF THE INVENTION

The present invention relates to hair fixative film compositions, wherein such films function as hair fixatives when dissolved in polar solvent and applied to the hair and/or are distributed through wet hair, and a method of fixing the hair by applying said hair fixative film compositions to the hair shafts. Another aspect of the invention relates to the addition of hair fixative films to existing products to achieve increased performance or add other additional properties to the products.

"Hair fixative film", as used herein, means a film which is either supported on a backing or unsupported, dissolves in polar solvent at room temperature, is applied and distributed through the hair by a consumer, and will hold the hair in a desired conformation after application. The hair fixative films may be single or multi-layered, embossed, textured and/or formed into different shapes.

"Dissolves in polar solvent" means that when the film is added to polar solvent, or polar solvent is added to the film, that the film breaks apart or combines with the polar solvent to form a solution or dispersion so as to enable the spread of the composition through hair. The wettability or dissolution rates may be modified by one skilled in the art to target a specific delivery profile.

"Hair fixative polymer", as used herein, means any film forming polymer that, when dissolved or dispersed and spread through hair, will fix the hair shafts in a given conformation and comprise natural and/or synthetic polymers and may be either anionic, cationic, nonionic, amphoteric, or betaine polymers and used either alone or in combination with other natural and/or synthetic polymers.

"Synthetic" as used herein means not derived in any part from a plant, animal or bacteria.

"Natural", as used herein, means derived or partially derived from a plant, animal or bacteria.

"Plasticizer", as used herein, means any material that will contribute to making a film composition less brittle and more flexible.

"Base", as used herein, means neutralizing agent and includes materials that will neutralize the free acid groups of a polymer.

"Dry", as used herein, means substantially free of water and other solvent, but does not mean the absence of water or solvent.

DETAILED DESCRIPTION OF THE INVENTION

The present invention relates to hair fixative film compositions comprising at least one hair fixative polymer, wherein such films function as hair fixatives when dissolved in polar solvent and applied to the hair or distributed directly through wet hair. Another aspect of the invention is a method of fixing the hair by applying said hair fixative films to hair shafts. Potential benefits of the invention may include the ability to combine ingredients incompatible in other applications, the ability to use high performance hair fixative polymers in non-spray applications, ecological friendliness, the ability to use high fixative polymer dosages, convenience of use, and small packaging sizes.

The film composition comprises at least one hair fixative polymer and may be selected from the group consisting of a synthetic polymer, a natural polymer, or a mixture thereof.

The hair fixative polymer will be present in the hair fixative film in an amount great enough to effectively fix the hair after application of the film to hair. In one embodiment, the hair fixative polymer is present in an amount from about 50 percent to about 100 percent based upon the weight of the hair fixative film. In another embodiment, the hair fixative polymer is present in an amount from about 60 percent to about 95 percent based upon the weight of the hair fixative film. In another embodiment, the hair fixative polymer is present in an amount from about 70 percent to about 90 percent based upon the weight of the hair fixative film. In another embodiment, the hair fixative polymer is present in an amount from about 75 to about 90 percent based upon the weight of the hair fixative film.

The following are examples of synthetic hair fixative polymers suitable for use in the present invention but in no way is meant to be limiting: from National Starch and Chemical Company, AMPHOMER and AMPHOMER LV-71 polymers (octylacrylamide/acrylates/butylaminoethyl methacrylate copolymer), AMPHOMER HC polymer (acrylates/octylacrylamide copolymer) BALANCE 0/55 and BALANCE CR polymers (acrylates copolymer), BALANCE 47 polymer (octylacrylamide/butylaminoethyl methacrylate copolymer), RESYN 28-2930 polymer (VA/crotonates/vinyl neodecanoate copolymer), RESYN 28-1310 polymer (VA/Crotonates copolymer), FLEXAN polymers (sodium polystyrene sulfonate), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) and STRUCTURE 3001 (acrylates/ceteth-20 itaconate copolymer); from ISP, OMNIREZ-2000 (PVM/MA half ethyl ester copolymer), GANEX P-904 (butylated PVP), GANEX V-216 (PVP/hexadecene copolymer) GANEX V-220 (PVP/eicosene copolymer), GANEX WP-660 (tricontanyl PVP), GANTREZ A425 (butyl ester of PVM/MA copolymer), GANTREZ AN-119 PVM/MA copolymer, GANTREZ ES 225 (ethyl ester of PVM/MA copolymer), GANTREZ ES425 (butyl ester of PVM/MA copolymer), GAFFIX VC-713 (vinyl caprolactam/PVP/dimethylaminoethyl methacrylate copolymer), GAFQUAT 755 (polyquaternium-11), GAFQUAT HS-100 (polyquaternium-28) AQUAFLEX XL-30 (Polyimide-1), AQUAFLEX SF-40 (PVP/Vinylcaprolactam/DMAPA Acrylates Copolymer), AQUAFLEX FX-64 (Isobutylene/Ethylmaleimide/Hydroxyethylmaleimide Copolymer), ALLIANZ LT-120 (Acrylates/C1-2 Succinates/Hydroxyacrylates Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), Copolymer Series (PVP/Dimethylaminoethylmethacrylate Copolymer), ADVANTAGE S and ADVANTAGE LCA (VinylcaprolactamNP/Dimethylaminoethyl Methacrylate Copolymer), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100P (t-butyl acrylate/ethyl acrylate/methacrylic acid), LUVIMER 36D (ethyl acrylate/t-butyl acrylate/methacrylic acid), LUVIQUAT HM-552 (polyquaternium-16), LUVIQUAT HOLD (polyquaternium-16), LUVISKOL K30 (PVP) LUVISKOL K90 (PVP), LUVISKOL VA 64 (PVPNA copolymer) LUVISKOL VA73W (PVPNA copolymer), LUVISKOL VA, LUVISET PUR (Polyurethane-1), LUVISET Clear (VP/MethacrylamideNinyl Imidazole Copolymer), LUVIFLEX SOFT (Acrylates Copolymer), ULTRAHOLD 8 (Acrylates/Acrylamide Copolymer), LUVISKOL Plus (Polyvinylcaprolactam), LUVIFLEX Silk (PEG/PPG-25/25 Dimethicone/Acrylates Copolymer); from Amerchol, AMERHOLD DR-25 (acrylic acid/methacrylic acid/acrylates/methacrylates); from Rohm&Haas, ACUDYNE 258 (acrylic acid/methacrylic acid/acrylates/methacrylates/hydroxy ester acrylates; from Mitsubishi and distributed by Clariant, DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers; from ONDEO Nalco, FIXOMER A-30 and FIXOMER N-28 (INCI names: methacrylic acid/sodium acrylamidomethyl propane sulfonate copolymer); from Noveon, FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base.

Natural fixative polymers suitable for use in the present invention include any single starch or combination of starches derived from a native source. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

Typical sources for the starches are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. As used herein, the term "waxy" is intended to include a starch containing at least about 95 percent by weight amylopectin and the term "high amylose" is intended to include a starch containing at least about 40 percent by weight amylose, more particularly at least about 70 percent amylose.

Native starches suitable for the present invention may be modified using any modification known in the art, including physical, chemical and/or enzymatic modifications, to obtain the desired film attributes.

Physically modified starches, such as sheared starches, or thermally-inhibited starches described in the family of patents represented by WO 95/04082 and resistant starches described in the family of patents represented by U.S. Pat. No. 5,593,503, may be suitable for use herein.

Chemically modified products are also intended to be included as the base material and include, without limitation, those which have been crosslinked, acetylated and organically esterified, hydroxyethylated and hydroxypropylated, phosphorylated and inorganically esterified, cationic, anionic, nonionic, amphoteric and zwitterionic, and succinate and substituted succinate derivatives thereof. Such modifications are known in the art, for example in Modified Starches: Properties and Uses, Ed. Wurzburg, CRC Press, Inc., Florida (1986).

Conversion products derived from any of the starches, including fluidity or thin-boiling starches prepared by oxidation, enzyme conversion, acid hydrolysis, heat and or acid dextrinization, thermal and or sheared products may also be useful herein.

Further suitable are pregelatinized starches which are known in the art and disclosed for example in U.S. Pat. Nos. 4,465,702, 5,037,929, 5,131,953, and 5,149,799. Conventional procedures for pregelatinizing starch are also known to those skilled in the art and described for example in Chapter XXII—"Production and Use of Pregelatinized Starch", Starch: Chemistry and Technology, Vol. III-Industrial Aspects, R. L. Whistler and E. F. Paschall, Editors, Academic Press, New York 1967.

Any starch or starch blend having suitable properties for use herein may be purified by any method known in the art to remove starch off colors that are native to the polysaccharide or created during processing. Suitable purification processes for treating starches are disclosed in the family of patents represented by EP 554 818 (Kasica, et al.). Alkali washing techniques, for starches intended for use in either granular or pregelatinized form, are also useful and described in the family of patents represented by U.S. Pat. No. 4,477,480 (Seidel) and U.S. Pat. No. 5,187,272 (Bertalan et al.).

Additional suitable starches are starches capable of emulsifying or encapsulating an active ingredient so that there is no need for additional encapsulating or emulsifying agents. Such starches include, without limitation, hydroxyalkylated starches such as hydroxypropylated or hydroxyethylated starches, and succinylated starches such as octenylsuccinylated or dodecylsuccinylated starches. In one embodiment, emulsifying or encapsulating starches are used so that a solution or dispersion of the film material (starch component, active agent, and optional additives) may be stored for later processing. The hydroxyalkylated starches have the added advantage of forming a softer film so that there is less or no need for a plasticizer.

To facilitate processing of the films, the starches may be partially converted to reduce the viscosity and allow for the production of a high solids starch dispersion/solution, such as a 30% solids starch dispersion/solution. Suitable starches in one embodiment are those with a viscosity of at least about 1000 cps at 10% solids and a viscosity of no more than about 100,000 cps at 30% solids.

In another embodiment, suitable starches have a flow viscosity of at least about 7 seconds. In another embodiment, suitable starches have flow viscosity of at least 10 seconds and no more than about 19 seconds. In yet another embodiment, suitable starches have a flow viscosity of no more than about 15 seconds. Flow viscosity, as used herein, is measured by the test defined in the Examples section, below.

The molecular weight of the starch is also important to its functionality in a film, particularly to film strength. For example, dextrins alone are not suitable in the present application.

The starch component may be a single modified or native starch, a blend of modified starches, or a blend of modified and native starches. Blends may be useful to lower the cost of the film or to more easily achieve a variety of desirable properties and functionalities.

Examples of commercial starches, with their INCI names, that may be used in the present invention comprise the following: from National Starch and Chemical Company, the AMAZE® polymer (corn starch modified), CELQUAT® LS-50 resin (polyquaternium-4/hydroxypropyl starch copolymer), STRUCTURE® XL polymer (hydroxypropyl starch phosphate), DRY FLO®PC lubricant (aluminum starch octenylsucinate), DRY FLO®AF lubricant (corn starch modified), DRY FLO® ELITE LL lubricant (aluminum starch octenylsuccinate (and) lauryl lysine), DRY FLO® ELITE BN lubricant (INCI name: aluminum starch octenylsuccinate (and) boron nitride), PURITY®21C starch (*zea mays* (corn) starch), TAPIOCA PURE (tapioca starch), thermally inhibited corn, potato, tapioca, high amylase, and waxy maize starches sold under the NOVATION trademark, and resistant starches sold under the HI-MAIZE trademark; from the Croda Company, CROSTYLE MFP (trimethyl quaternized maize starch); from ONDEO Nalco, SENSOMER CI-50 (starch hydroxypropyltrimonium chloride).

The natural polymer also may comprise without limitation a cellulosic material such as carboxymethyl cellulose, hydroxypropyl cellulose, microcrystalline cellulose, ethylcellulose, cellulose acetate phthalate, cationic cellulose derivatives such as polyquaternium-4 (CELQUAT L-200 and CELQUAT H-100 polymers from National Starch and Chemical Company) and polyquaternium-10 (CELQUAT SC-240C and CELQUAT 230M polymers from National Starch and Chemical Company), or a gum, xanthan (such as the AMAZE™XT polymer from National Starch and Chemical Company), pullulan, hydrocolloids, carageenan, alginate, casein, gelatin, and solubilized proteins.

In films containing both synthetic and natural hair fixative polymers, the ratio of synthetic to natural hair fixative polymer based on the weight of the total fixative polymer is from about 5:95 to about 95:5; in another embodiment from about 20:80 to about 75:25; in another embodiment from about 25:75 to about 60:40; in another embodiment from about 30:70 to about 55:45; in another embodiment from about 35:65 to about 42:58; in another embodiment from about 29:71 to about 33:67.

The hair fixative films of the invention contain a hair fixative polymer or blend of different hair fixative polymers. One skilled in the art can add additional materials to the hair fixative film compositions to modify the performance or physical properties of the film. For instance, one skilled in the art knows that many synthetic fixative polymers may require the addition of a base and/or plasticizer to make the films soluble, less brittle, and/or to optimize on-hair performance. Plasticizing agents are also useful to add to the flexibility of films containing natural or synthetic fixative polymers. The film should be strong, yet flexible and should not be overly brittle. It must be blocking and moisture resistant so that it does not adhere to itself, yet able to dissolve or disintegrate quickly when exposed to water or other polar solvent such as when wetted in the hand.

Such plasticizing agents are known in the art and include without limitation dimethicone copolyols, polyols, polycarboxylic acids, and polyesters. Examples of useful dimethicone copolyols include, but are not limited to PEG-12 Dimethicone, PEG/PPG-18/18 Dimethicone, and PPG-12 Dimethicone. Examples of useful polyols include, but are not limited to ethylene glycol, propylene glycol, sugar alcohols such as sorbitol, manitol, maltitol, lactitol; mono-di- and oligosaccharides such as fructose, glucose, sucrose, maltose, lactose, and high fructose corn syrup solids and ascorbic acid. Examples of polycarboxylic acids include, but are not limited to, citric acid, maleic acid, succinic acid, polyacrylic acid, and polymaleic acid. Examples of polyesters include, but are not limited to, glycerol triacetate, acetylated-monoglyceride, diethyl phthalate, triethyl citrate, tributyl citrate, acetyl triethyl citrate, acetyl tributyl citrate.

Other examples of plasticizers include, but are not limited to mineral oils, vegetable oils, triglycerides, lanolins and their derivatives, unsaturated fatty acids and their derivatives, silicones, and some emollients; humectants such as glycerol, sorbitol, lactates (including but not limited to sodium, ammonium, and potassium salts), polyols (e.g. propylene glycol), polyethylene glycol (200-600), and Sorbeth-30; natural moisturizing factors (NMFs) such as urea, lactic acid, and sodium pyrrolidone carboxylic acid (PCA); liposomes, natural and vegetal moisturizing agents such as glycerol, serine, chitosan PCA, sodium hyaluronate, hyaluronic acid, microsponges, soluble collagen, modified protein, monosodium L-glutamate, lecithins and phospholipids and their derivatives; alpha and beta hydroxy acids such as glycolic acid, lactic acid, citric acid, maleic acid and salicylic acid; polymeric plasticizers such as polysaccharides and their derivatives, polyacrylates, and polyquaterniums; proteins and amino acids such as glutamic acid, aspartic acid, and lysine.

The plasticizers will be present in a plasticizing effective amount. In one embodiment, the plasticizer will be present in the hair fixative film in an amount from about 0 to about 30 percent based on the weight of the dry film composition. In yet another embodiment, the plasticizer will be present in an amount from about 5 to about 15 percent based on the weight of the dry film composition. In hair fixative films in which the natural fixative is at least 60% (wt/wt) based upon the total fixative, a plasticizer may be present in an amount greater than 15 percent based upon the weight of the natural polymer, but not greater than about 30 percent based upon the weight of the dry film; in another embodiment, greater than 17 percent based upon the total weight of the natural polymer and less than about 30 percent based upon the weight of the total dry film composition; and in yet another embodiment, greater than 20 percent based upon the total weight of the natural polymer and less than about 30 percent based upon the weight of the total dry film composition. Some plasticizers may be added to the solution to be dried to make the hair fixative film at a dosage above the desired end dosage, and a portion of the plasticizer, the excess portion, may then be driven off with heat during film formation. One skilled in the art would know how to adjust the plasticizer to balance film properties.

As known in the art, those hair fixative polymers which contain acidic groups and are insoluble in water are usually used in their neutralized, water-soluble or water dispersible form.

Suitable neutralizing agents which may be included alone or in combination in the composition of the present invention include, but are not limited to, alkyl monoamines containing from about 2 to 22 carbon atoms such as triethylamine, stearylamine and laurylamine, and amino alcohols such as triethanolamine, 2-amino-2-methyl-1,3-propanediol and 2-amino-2-methyl-1-propanol, and inorganic neutralizers such as sodium hydroxide and potassium hydroxide. Other combinations of useful neutralizing agents are described in U.S. Pat. No. 4,874,604 to Sramek.

With polymers requiring neutralization, the neutralizer will be present in an amount effective to neutralize a percentage of the polymer's free acid groups and render the polymer water-soluble or water-dispersible. In one embodiment, the neutralizer will be present in an amount sufficient to neutralize the free acid groups of the fixative polymer from about 8 percent to 100 percent neutralization. In another embodiment, the free acid groups of the fixative polymer will be neutralized from about 25 percent to 100 percent. In another embodiment, the free acid groups of the fixative polymer will be neutralized from about 50 percent to 100 percent. In another embodiment, the free acid groups of the fixative polymer will be neutralized from about 70 percent to 100 percent. In yet another embodiment, the free acid groups of the fixative polymer will be neutralized from about 80 to 100 percent.

The base may also be used in excess of 100 percent neutralization to increase the solution pH or to plasticize the resin in addition to neutralization of the polymer acid groups.

The hair fixative film composition may also include other optional film forming and hair fixative ingredients known in the art. These optional ingredients include, without limitation, thickeners, emulsifiers, aesthetic modifiers, UV filters, humectants (such as hydroxyethyl urea, available from Nationla Starch and Chemical Company under the trademark HYDROVANCE), lubricants, skin whitening ingredients, silicones, powders, deviscosifying agents, moisturizers, emollients, solvents, chelating agents, vitamins, antioxidants, botanical extracts, pH adjusting agents, preservatives, fragrances, waterproofing agents, active ingredients (anti-aging agents, firming or toning agents, etc.), dyes, pigments, colors, polymers, conditioning agents, rheology modifiers, surfactants, opacifiers, foaming agents, heat generating agents and/or effervescing agents, glitter and decorative beads and shapes.

The effervescing agents may be one or more materials that effervesce when coming into contact with water. In one embodiment, the effervescent element of the film is comprised of two components. Suitable fist components comprise any acids present in dry solid form such as $C_2$-$C_{20}$ organic mono- and poly-carboxylic acids. In another embodiment, the first component may be alpha- and beta-hydroxycarboxylic acids; $C_2$-C20 organosulfur acids such as toluene sulfonic acid; and peroxides such as hydrogen peroxide. In one embodiment hydroxycarboxylic acids comprise adipic, gutaric, succinic, tartaric, malic, maleic, lactic, salicylic as well as acid forming lactones such as gluconolactone and glucarolactone. In another embodiment, the acid is citric acid. Also suitable as the acid material are water soluble synthetic or natural polymers such as polyacrylates (e.g., encapsulating polyacrylic acid), cellulosic gums, polyurethane and polyoxyalkalene polymers. The term "acid" is meant to include any substance which when dissolved in deionized water at 1% concentration will have a pH of less than 7; in another embodiment less than 6.5; in another embodiment less than 5. The acids in one embodiment are in the solid form at 25° C., (i.e., having melting points no less than 25° C.). Concentration of the acid should range from about 0.5 to about 80 percent based on the final weight of the fixative film; in another embodiment from about 10 to about 65 percent; in another embodiment from about 20 to 40 percent.

Suitable second components of the effervescent element comprise alkaline materials. An alkaline material is a substance which can generate a gas such as carbon dioxide, nitrogen or oxygen (i.e., effervesce), when contacted with water and the acidic material of the first component. Suitable alkaline materials comprise anhydrous salts of carbonates and bicarbonates and alkaline peroxides. In one embodiment, the alkaline material is sodium or potassium bicarbonate. Amounts of alkaline material may range from about 1 to about 40 percent based upon the weight of the fixative film; in another embodiment from about 5 to 35 percent; in another embodiment from about 15 to about 30 percent; in another embodiment from about 25 to about 35 percent.

The acid and alkaline components of the effervescing element may be physically separated until combined with water. Such methods of separation comprise formulating a bi-layer film wherein one layer contains the acid component and the other layer contains the alkaline component. Another method of physical separation comprises encapsulation of at least one component in a third material. Such methods of producing bi-layer films and encapsulation of acid or basic materials are known in the art.

The heat-generating component of a film may be one material or a combination of more than one material that generates heat when coming into contact with water. Examples of heat-generating combinations include combinations of acids and bases. In another embodiment, the heat-generating combination is of an oxidizing reagent and a reducing agent. Such oxidizing and reducing agents may be selected broadly from the various compounds of this nature available. Examples of oxidizing agents comprise chlorates, perchlorates, permanganates, persulfates, peroxides, nitrates, metal oxides, such as copper oxide, lead oxide, and iron oxide, and perborates. In one embodiment, the oxidizing agent is selected from the group consisting of hydrogen peroxide, urea peroxide, sodium peroxide, sodium perborate, sodium persulfate, ammonium persulfate, potassium persulfate, and mixtures of any of two or more of the foregoing. Examples of reducing agents comprise magnesium, zinc, aluminum and iron; sulfites, thio-sulfates, thioureas, imidazolinethiones, thiotrazoles, thiopyridines, thio-pyrimidines, thiols, thio-acids, sulfoxides, xanthates, ortho- and para-polyhydroxy benzenes, aldehydes, and glycols.

The oxidizing and reducing agents may be physically separated until combined with water. Such methods of separation comprise formulating a bi-layer film wherein one layer contains the oxidizing component and the other layer contains the reducing component. Another method of physical separation includes encapsulation of at least one component in a third material.

Single components that generate heat when combined with water are those having an appreciable heat of solution or dilution in water, e.g. the combination of water and ethylene glycol and the combination of water and salts such as aluminum sulfate, calcium chloride, copper sulfate, ferric chloride, magnesium chloride, magnesium sulfate, etc. In one embodiment, the single heat-generating component may range from about 1 to about 40 percent based upon the weight of the fixative film; in another embodiment from about 5 to 35 percent; in another embodiment from about 15 to about 30 percent; in another embodiment from about 25 to about 35 percent The hair fixative films of the present invention are formed by techniques known in the industry. For example, the hair fixative may be dispersed with the other film components in water or other solvent and dried into film form. In the alternative, the fixative polymer and other dry components may be blended and then dispersed with any additional film components in water or other solvent and dried into film form. Films may be formed from such dispersions or solutions by shaping it into a solidified form of a suitable thickness by any technique known in the art including, but not limited to, wet casting, freeze-drying, and extrusion molding. The dispersion or solution may also be directly coated or sprayed onto another product and dried to form a film.

In one embodiment, the films of the present invention are processed by preparing a coating formulation by making a solution or dispersion of the film components, applying the mixture to a substrate, using knife, bar or extrusion die coating methods, drying the coated substrate to remove the majority of the solvent, and removing the film from the substrate. Suitable substrates include, but are not limited to, silicone elastomers, metal foils and metalized polyfoils, composite foils or films containing polytetrafluoroethylene materials or equivalents thereof, polyether block amide copolymers, polyurethane, polyvinylidene, polyester, and other such materials useful in the art as releasable substrates. The hair fixative film may be dried at standard temperature and pressure or elevated temperature and/or pressure, or lower temperature and/or pressure compared to standard conditions.

Dissolution rate is determined by measuring the time it takes a square inch of film to disintegrate in a beaker of polar solvent. In one embodiment, the hair fixative film will disintegrate in 25° C. water in less than about 15 minutes. In another embodiment, the hair fixative film will disintegrate in 25° C. water in less than 10 minutes. In another embodiment, the hair fixative film will disintegrate in 25° C. water in less than 5 minutes. In another embodiment, the hair fixative film will disintegrate in 25° C. water in less than 2.5 minutes. In another embodiment, the hair fixative film will disintegrate in 25° C. water in less than 1 minutes. In another embodiment, the hair fixative film will disintegrate in 25° C. water in less than 45 seconds. In another embodiment, the hair fixative film will disintegrate in 25° C. water in less than 30 seconds. In another embodiment, the hair fixative film will dissolve in 25° C. ethanol in less than 5 minutes. In another embodiment, the hair fixative film will disintegrate in 25° C. ethanol in less than 2.5 minutes. In another embodiment, the hair fixative film will disintegrate in 25° C. ethanol in less than 1 minutes. In another embodiment, the hair fixative film will disintegrate in 25° C. ethanol in less than 45 seconds. In another embodiment, the hair fixative film will disintegrate in 25° C. ethanol in less than 30 seconds.

The films may not be completely dried in that some degree of water or other solvent remains. The amount of solvent present in the film may be controlled to obtain desired functionality. For example, more solvent typically results in a more flexible film, while too much solvent may result in a film that will block and be tacky. Some solvent is generally in the hair fixative film as used. In one embodiment, the remaining solvent in the fixative film may be in the range from about 0 to about 25 percent, based on the weight of the film; in another embodiment, from about 1 to about 20 percent solvent remains; in another embodiment, from about 5 to 16 percent solvent remains; in another embodiment, about 10 to 15 percent solvent remains.

The film thickness may be in the range of about 1 to 500 microns, and in one embodiment the film has a thickness from about 25 to about 100 microns. In another embodiment, the film has a thickness from about 25 to 60 microns, and in yet another embodiment the film has a thickness from about 25 to about 50 microns.

The resultant films are lightweight and easy to carry. They are sufficiently strong and apparently flexible so as to be easily dispensable and handled.

The films exhibit moisture and blocking resistance, yet are wetted when exposed to water or a polar solvent followed by rapid dissolution and/or disintegration. The wettability and dissolution rates of the hair fixative films may be modified by one skilled in the art to target a specific delivery profile. For example, more rapid dissolution of carboxylated hair fixative polymers may be achieved using neutralization and/or plasticization. Neutralization of carboxylic groups of hair fixative polymers creates charged groups along the polymer backbone wherever a carboxyl group is neutralized. The charged polar groups make these sections of the polymer more soluble in polar solvents than if these carboxyl groups were not neutralized.

The hair fixative films of the present invention provide excellent high humidity resistance to the hair style. In one embodiment of the invention, the fixative film will give an average high humidity curl retention of greater than 15 percent after 2 hrs. In another embodiment the hair fixative films give a high humidity curl retention greater than 20 percent after 2 hrs. In another embodiment, the hair fixative films give a high humidity curl retention greater than 30 percent after 2 hrs. In another embodiment, the hair fixative films give a high humidity curl retention greater than 60 percent after 2 hrs. "High humidity curl retention", as used herein, is measured by the test defined in the Examples section below. One skilled in the art would know how to select hair fixative polymers or formulate to provide more or less humidity resistance to a hair fixative film.

The hair fixative films of the present invention also provide stiffness to the hair. In one embodiment, the hair stiffness is from about 0.004 Joules to about 0.030 Joules. In another embodiment, the hair stiffness is from about 0.008 Joules to about 0.030 Joules. In another embodiment, the hair stiffness is from about 0.012 Joules to about 0.025 Joules. In another embodiment, the hair stiffness is from about 0.015 Joules to about 0.025 Joules. "Stiffness", as used herein, is measured by the standard test defined in the Examples section below.

The hair fixative films of the present invention permit the use of high performance polymers that can not be used together in other applications. The formulation of these polymers into a hair fixative film gives a novel, fun application and overcomes some of the limitations associated with other applications. For example, some anionic and cationic polymers may be combined and formed into films in ratios that would form an insoluble precipitate in aqueous solutions or have unacceptable rheology in gel or spray applications. In another example, PVP and sulfonated polystyrene forms a gel that is so viscous at high concentrations that it may not be used in traditional hair fixative spray applications, but this combination may be formed into a film and used as a hair fixative in the present invention.

A user of the personal care composition may apply the film to the hair in a number of different ways. One method of application comprises wetting the hands, placing the composition in the hands, distributing the film over the hands and then applying by passing the hands through the hair. In an alternate embodiment, the user may place the film directly on wet hair and distribute the film as desired through their hair. In another embodiment, the film may be placed directly in the hands and then wetted and distributed throughout the hair. Any other similar application method may be used.

In another method of application of the hair fixative films of the present invention, the hair fixative film may be dissolved or dispersed in another application type to add or increase the hair fixative properties of the application. For instance, in one embodiment, the hair fixative film may be added to an existing hair fixative gel to increase the holding power of the gel. In another embodiment, the hair fixative film is added to a non-aerosol hair spray to increase the holding power. In another embodiment, the hair fixative film is added to a curl defining lotion to add hair fixative properties.

In another method of application of the hair fixative films of the present invention, the hair fixative film may be applied to the hair by adding another product to a hair fixative film to dissolve or disperse the hair fixative film and then apply to the hair. For instance, in one embodiment, a quantity of hair gel may be added to a film in the hand and mixed in the hand to dissolve or disperse the film so that it may be then applied to the hair together. In another embodiment, a hair spray is sprayed onto the film in the hand then mixed by rubbing with the hands and applied to the hair together. In another embodiment, a quantity of a hair product containing a polar solvent such as a lotion, mousse, hair wax, pomade, or shine product may be added to the film to disperse or dissolve the film and then applied to the hair together.

EXAMPLES

The following examples are presented to further illustrate and explain the present invention and should not be taken as limiting in any regard.

All percents used are on a weight/weight basis. In the examples below, the following materials in Table 1 are used:

TABLE 1

| Tradename | Chemical or CTFA Name | Function |
| --- | --- | --- |
| AMP 95 | Aminomethyl Propanol (95% in water) | Neutralizer |
| CELQUAT ® LS-50 resin | Polyquaternium-4/Hydroxypropyl Starch Copolymer | Fixative |
| AMAZE ® polymer | Corn starch Modified | Fixative |
| PVP K-90 | Polyvinylpyrrolidone | Fixative |
| AMPHOMER ® polymer | Octylacrylamide/acrylates/ butylaminoethyl methacrylate copolymer | Fixative |
| RESYN ® 28-2930 polymer | VA/Crotonates/Vinyl Neodecanoate Copolymer | Fixative |
| DynamX ™ polymer | Polyurethane-14 (and) AMP-Acrylates Copolymer | Fixative |
| LUVISET PUR | Polyurethane-1 | Fixative |
| LUVITEC 64 Pulver | PVP/VA | Fixative |
| LUVISKOL 73W | PVP/VA | Fixative |
|  | Propylene Glycol | Plasticizer |
| Dow Corning 193 Surfactant | PEG-12 Dimethicone | Plasticizer |
|  | Dipropylene Glycol | Plasticizer |
| CROPEPTIDE W | Hydrolyzed Wheat Protein | Plasticizer |
| GLYDANT Plus | DMDM Hydantoin (and) Iodopropynyl Butylcarbamate | Preservative |

In the examples below, the starches used are as follows:

Acetylated=acetylated (5% treatment) high amylose (70%) corn starch commercially available from National Starch and Chemical Company (Bridgewater, N.J., USA).

Converted=mannox converted waxy corn starch commercially available from National Starch and Chemical Company (Bridgewater, N.J., USA).

Corn=native corn starch commercially available from National Starch and Chemical Company (Bridgewater, N.J., USA).

OSA waxy 1=mannox degraded octenylsuccinated waxy corn starch commercially available from National Starch and Chemical Company (Bridgewater, N.J., USA).

PO waxy 1=Hydroxypropylated (8.5% treatment) waxy corn starch with a water fluidity of 35* commercially available from National Starch and Chemical Company (Bridgewater, N.J., USA).

PO waxy 2=Agglomerated hydroxypropylated (8.5% treatment) waxy corn starch with a water fluidity of 35* commercially available from National Starch and Chemical Company (Bridgewater, N.J., USA).

PO waxy 3—Hydroxypropylated (8.5% treatment) waxy corn starch with a water fluidity of 15* commercially available from National Starch and Chemical Company (Bridgewater, N.J., USA).

Pullulan=pullulan (grade PF-20, molecular weight of 200,000) commercially available from Hayishibara Co., Ltd. (Japan).

Tapioca=native tapioca starch, commercially available from National Starch and Chemical Company (Bridgewater, N.J., USA).

Example 1

Procedures

In the examples below, the procedures used are as follows:

Film Casting: films were cast by drawing down the solution/dispersion using a Braive Laboratory Bar Coater, either dried at room temperature overnight or dried in an oven at 250° F. (121° C.).

Blocking resistance: films are stacked on top of each other, conditioned for 24 hours at 104° F. (40° C.) and 75% relative humidity, then pulled apart to see whether or not they block (adhere).

Dissolution time: dissolution time is determined by measuring the time, in seconds, that it takes for a square inch (6.45 cm²) of film to disintegrate in a beaker of polar solvent at 25° C.

Flow Viscosity: flow viscosity is measured as follows. The starch is slurried in water and jet cooked at 149° C. until fully gelatinized. The solids are adjusted to 5% (w/w). the temperature of the starch solution is controlled at 22° C. A total of 100 ml of the starch dispersion is measured into a graduated cylinder. It is then poured into a calibrated funnel while using a finger to close the orifice. A small amount is allowed to flow into the graduated to remove any trapped air, and the balance is poured back into the funnel. The graduated cylinder is then inverted over the funnel so that the contents draw (flow) into the funnel while the sample is running. Using a timer, the time required for the 100 ml sample to flow through the apex of the funnel is recorded.

The glass portion of the funnel is a standard 58°, thick-wall, resistance glass funnel whose top diameter is about 9 to 10 cm with the inside diameter of the stem being approximate length of 2.86 cm form the apex, carefully firepolished, and refitted with a long stainless steel tip which is 5.08 cm long with an outside diameter of 0.9525 cm. The interior diameter of the steel tip is 0.5951 cm at the upper end where it is attached to the glass stem; it is 0.4445 cm at the outflow end, with the restriction in the width occurring at about 2.54 cm from the ends. The steel tip is attached to the glass funnel by means of a Teflon tube. The funnel is calibrated so as to allow 100 ml of water to go through in 6 seconds using the above procedure.

Stiffness: "stiffness" is the amount of work required to deflect a hair swatch 10 mm at a rate of 50 mm/min. Stiffness is measure using the following procedure. Five 6 inch (15.24 cm) virgin brown hair swatches are used for each sample to be tested. Polymer solids are set at 0.75 percent for each formulation and 2 grams of aqueous polymer solution is applied to each hair swatch. Each swatch is tared and then dipped into the aqueous polymer solution so that it is wetted thouroughly. The swatches are then drawn between the thumb and forefinger and blotted with a paper towel until the weight of each swatch is 2.0 grams plus or minus 0.1 grams more than the tare weight. The excess weight is the weight of the solution applied to the swatch and equates to 0.015 grams of polymer applied to the hair swatch. After the solution is applied, the swatches are allowed to air dry in a constant temperature and humidity room, maintained at 72° F. (22.2° C.) and 50 percent relative humidity, prior to testing.

The swatches are tested the next day using a Diastron MTT 160 miniature tensile tester with a stiffness testing jig available from the manufacturer of the instrument. Each hair swatch is then laid across two lower horizontal prongs (or bars) separated by 10 cm and running perpendicular to direction the hair is laid to be evaluated one swatch at a time. The Diastron instrument then applies a measured force, in Newtons, with a 1 cm diameter horizontal bar perpendicular to the horizontal swatch and between the two lower bars to bend the swatch a distance of 10 mm. The work, in Joules, is the stiffness of the hair swatch with a certain composition applied to the hair swatch. The stiffness for the five 6 inch (15.24 cm) swatches are then recorded and analyzed statistically to determine an average stiffness for the sample tested.

High Humidity Curl Retention: it is known in the art that high humidity curl retention is a measurement of how well a fixative formulation will maintain hair in a given style in high humidity conditions and is a standard and important test of a hair fixatives performance. The curl retention properties of hair fixative films of the present invention are measured using this procedure and compared to each other. The test is conducted at 72° F. (22° C.) and 90 percent Relative Humidity over a period of 2 hours. The procedure allows for statistical analysis of formulation variables. The percentage curl retention is calculated by the following formula: Curl Retention $\% = 100 \times (L - L_t)/(L - L_0)$, where L=length of hair fully extended, $L_0$=initial curl length, $L_t$=curl length at a given time t.

The test is performed on 10 inch (25.4 cm) long×2 gram tresses of European virgin brown hair (9 replicate tresses per sample). Cleaned wet hair tresses are combed through to remove tangles and excess water is removed. Two grams of 0.75 percent hair fixative film solution is applied to each tress, gently "worked into" the hair tress and combed through. Curls of hair are made using a ½ inch (1.27 cm) diameter Teflon mandrel, placed on a tray and dried in an oven overnight. The curls are suspended from the bound end of the tress on graduated transparent curl retention boards. An initial curl length reading is taken before placing boards and curls into the constant temperature and humidity chamber for exposure. Then curl lengths are recorded at 15 minutes, 30 minutes, 60 minutes, 90 minutes and 2 hours. Curl retention averages are then calculated. The curl retention results after 2 hours are tabulated in Table 6. The results demonstrate that all the hair fixative film compositions provide some curl retention properties; however, the high performance polymers provide dramatically better humidity resistance. One skilled in the art would be able modify the High Humidity Curl Retention performance of a film by choice of polymer type and amount choice of plasticizer type and amount included in the formulation.

Example 2

Comparison of Various Starch Films

Films were made of a variety of starches and pullulan and the films were tested subjectively for flexibility, clarity, tack, blocking resistance and objectively for dissolution time. The results are shown in Table 2 below.

TABLE 2

| Starch/ Pullulan | Apparent flexibility | Clarity | Tack | Blocking | Dissolution Time (sec) | Flow Viscosity (sec) |
|---|---|---|---|---|---|---|
| Pullulan | Flexible | Clear | None | None | 9 | — |
| Po waxy 1 | Flexible | Clear | None | None | 6.5 | 12.1 |
| Corn | Flexible | Hazy | None | None | >120 | 17.2 |
| Tapioca | Flexible | Clear | None | None | 83 | 35.0 |
| Acetylated | Flexible | Hazy | None | None | >120 | 11.9 |
| PO waxy 3 | Flexible | Clear | None | None | 36 | 19.6 |
| OSA waxy 1 | Flexible | Clear | None | None | 42 | 10.1 |
| Converted | Flexible | Clear | None | None | 8.5 | 10.1 |
| PO waxy 2:Pullulan 90:10 | Flexible | Clear | None | None | 13.5 | — |
| PO waxy 2:Corn 90:10 | Flexible | Hazy | None | None | 7.5 | — |

Example 3

Hair Fixative Film Ingredient Compatibility, Plasticizer Levels, and Use as Hair Fixatives Tables 3, 4 and 5, below, contain representative formulations embodying the present invention where the ingredients are combined and/or mixed to form a liquid product composition which then may be dried at ambient temperature and pressure, at elevated or lower temperature, and/or at elevated or lower pressure to form the hair fixative film.

TABLE 3

| Ingredients | Formula # and Weight (grams) | | | | | |
|---|---|---|---|---|---|---|
| | 1 | 2 | 3 | 4 | 5 | 6 |
| AMP 95 | — | — | 6.4 | 0.9 | 4.6 | — |
| CELQUAT LS-50 resin | 21.3 | — | — | — | — | — |
| AMAZE polymer | — | 15.5 | — | 23.6 | — | 23.8 |
| PVP K-90 | — | 7.5 | — | 5.1 | — | — |
| AMPHOMER polymer | — | — | 37.4 | 5.1 | — | — |
| DynamX polymer | — | — | — | — | — | 83.8 |
| Luvitec 64 Pulver | — | — | — | — | — | — |
| RESYN 28-2930 polymer | — | — | — | — | 50.0 | — |
| Propylene Glycol | 1.3 | — | 4.3 | 6.2 | 5.6 | 2.5 |
| DOW CORNING 193 Surfactant | 2.5 | — | 1.1 | — | — | — |
| Dipropylene Glycol | — | 1.3 | — | — | — | — |
| CROPEPTIDE W | — | 0.8 | — | 1.2 | — | — |
| Water | 225 | 225 | 201 | 183.0 | 189.9 | 140 |

TABLE 4

| Ingredients | Formula # and Weight (grams) | | | | | |
|---|---|---|---|---|---|---|
| | 7 | 8 | 9 | 10 | 11 | 12 |
| CELQUAT LS-50 resin | 21.0 | — | — | — | — | — |
| LUVITEC 64 pulver | 9.7 | — | — | — | — | — |
| AMPHOMER polymer | — | 3.8 | 37.4 | — | — | 3.4 |
| AMAZE polymer | — | 22.9 | — | — | — | 21.5 |
| PVP K-90 | — | 11.5 | — | — | 47.5 | 10.2 |
| BALANCE CR polymer | — | — | — | 100.0 | — | — |
| AMP 95 | 9.7 | 0.7 | 6.3 | 6.1 | — | 0.6 |
| Propylene glycol | 2.5 | 4.4 | 6.6 | 5.0 | — | 11.9 |
| Dipropylene glycol | — | — | — | — | 5.3 | — |
| CROPEPTIDE W | — | 1.3 | — | — | — | — |
| Water | 216.8 | 180.5 | 199.7 | 138.9 | 197.2 | 202.4 |

TABLE 5

| Ingredients | Formula # and Weight (grams) | | | | |
|---|---|---|---|---|---|
| | 13 | 14 | 15 | 16 | 17 |
| CELQUAT LS-50 resin | — | 21.0 | 21.0 | — | — |
| LUVITEC 64 Pulver | — | 9.7 | 9.7 | — | — |
| AMPHOMER polymer | 3.4 | — | — | 3.4 | 3.4 |
| AMAZE polymer | 21.4 | — | — | 21.5 | 21.5 |
| PVP K-90 | 10.1 | — | — | 10.2 | 10.2 |
| AMP 95 | 0.6 | — | — | 0.6 | 0.6 |
| Propylene glycol | 15.2 | 10.3 | 13.2 | 3.9 | 6.2 |
| Water | 199.1 | 209.0 | 206.0 | 210.7 | 208.2 |

Formulation 1-17's ingredients were combined and formed acceptable films after drying.

Formulation 1 demonstrates the ability to formulate starch and cationic cellulose together where the polymers would separate over time if kept in solution and demonstrates the use of dimethicone copolyol and propylene glycol as plasticizer.

Formulation 2 demonstrates the ability to formulate nonionic modified starch and nonionic synthetic into an acceptable film and demonstrates the use of the plasticizers dipropylene glycol and CROPEPTIDE W.

Formulation 3 demonstrates the use of an amphoteric synthetic polymer and neutralization in combination with plasticizers to improve film aesthetics.

Formulation 4 demonstrates the combination of an amphoteric synthetic polymer in combination with a nonionic starch and synthetic polymer.

Formulation 5 demonstrates the use of an anionic synthetic polymer neutralized with AMP and plasticized.

Formulation 6 demonstrates the use of a nonionic modified starch in combination with a polyurethane and a neutralized acrylate polymer and plasticizer.

Formulation 7 demonstrates the combination of cationic cellulose, modified starch, and an nonionic synthetic copolymer and plasticizer where a solution would separate.

Formulation 8 demonstrates the combination of a synthetic amphoteric polymer, a nonionic modified starch, and a nonionic synthetic polymer with a base and a plasticizer.

Formulation 9 demonstrates a neutralized synthetic amphoteric polymer used as the sole polymer to form an acceptable hair fixative film.

Formulation 10 demonstrates the use of a neutralized anionic synthetic acrylate polymer as the sole polymer to form an acceptable hair fixative film.

Formulation 11 demonstrates the use of a nonionic synthetic polymer as the sole polymer to form a hair fixative film.

Formulation 12 demonstrates the combination of a neutralized amphoteric polymer, a nonionic modified starch, a nonionic synthetic polymer and propylene glycol as plasticizer at the given level.

Formulation 13 demonstrates the combination of a neutralized amphoteric polymer, a nonionic modified starch, a nonionic synthetic polymer, and propylene glycol plasticizer at the given level.

Formulation 14 demonstrates the combination of a nonionic modified starch, a nonionic synthetic copolymer, a cationic cellulose with propylene glycol as plasticizer at the given level.

Formulation 15 demonstrates the combination of a nonionic modified starch, a cationic cellulose, a nonionic synthetic copolymer and propylene glycol as plasticizer at the given level.

Formulations 16 and 17 demonstrate the formulation of an amphoteric synthetic polymer neutralized with AMP-95, a nonionic synthetic polymer, a natural polymer and two different levels of propylene glycol as plasticizer.

The films from formulas 1 to 17 were then evaluated on hair swatches for hair fixing properties. All formulations were found to have excellent hair fixative properties such as good hold, stiffness, dry comb properties, webbing, spring, and feel and were acceptable as styling products.

Example 4

Hair Swatch Stiffness

The following formulations in Table 6 were evaluated for film stiffness using the procedure described above in Example 1. The stiffness value for each formulation is reported below the formulation ingredient dosages.

TABLE 6

| Ingredients | 1 | 2 | 3 | 4* | 5* | 6* | 7 |
|---|---|---|---|---|---|---|---|
| RESYN 28-2930 polymer | — | 1.88 | — | — | — | — | — |
| LUVISKOL 73W | — | — | — | 3.67 | — | — | — |
| AMPHOMER polymer | 1.87 | — | — | — | — | — | — |
| AMAZE polymer | — | — | — | — | — | — | 1.87 |
| PVP K-90 | — | — | 1.88 | — | — | — | — |
| BALANCE CR polymer | — | — | — | — | 4.17 | — | — |
| LUVISET PUR | — | — | — | — | — | 6.23 | — |
| AMP 95 | 0.32 | 0.19 | — | — | 0.25 | — | — |
| Propylene glycol | 0.33 | 0.10 | 0.10 | 0.33 | 0.10 | 0.21 | 0.21 |
| GLYDANT Plus | 1.25 | 1.25 | 1.25 | 1.25 | 1.25 | 1.25 | 1.25 |
| Water | 246.2 | 246.6 | 246.8 | 244.7 | 244.2 | 242.3 | 246.7 |
| Formulation Stiffness (Joules) | .008 | .004 | .012 | .004 | .008 | .007 | .015 |

*Polymer amounts adjusted for the percent solids of the product as supplied. Formulations 1–7 in Table 6 demonstrate that a formulation may be modified to provide different stiffness. These test results correspond directly with the stiff feel of the formulation on the hair when evaluated by human touch.

Example 4

Performance of Hair Fixative Films in High Humidity Curl Retention

The following formulations were prepared and tested for performance in High Humidity Curl Retention (HHCR) using the procedure described above in Example 1 and made into successful films. The formulations tested for HHCR are tabulated in Table 7 below, and the average High Humidity Curl Retention test results for each formula is noted at the end of the table below the ingredient dosages for each formulation.

TABLE 7

| Ingredients | 1 | 2 | 3 | 4* | 5* | 6* | 7 |
|---|---|---|---|---|---|---|---|
| RESYN 28-2930 polymer | — | 1.88 | — | — | — | — | — |
| LUVISKIL 73W | — | — | — | 3.67 | — | — | — |
| AMPHOMER polymer | 1.87 | — | — | — | — | — | — |
| AMAZE polymer | — | — | — | — | — | — | 1.87 |
| PVP K-90 | — | — | 1.88 | — | — | — | — |
| BALANCE CR polymer | — | — | — | — | 4.17 | — | — |
| LUVISET PUR | — | — | — | — | — | 6.23 | — |
| AMP 95 | 0.32 | 0.19 | — | — | 0.25 | — | — |
| Propylene glycol | 0.33 | 0.10 | 0.10 | 0.33 | 0.10 | 0.21 | 0.21 |
| GLYDANT Plus | 1.25 | 1.25 | 1.25 | 1.25 | 1.25 | 1.25 | 1.25 |
| Water | 246.2 | 246.6 | 246.8 | 244.7 | 244.2 | 242.3 | 246.7 |
| Average HHCR(%) | 46.14 | 24.16 | 18.27 | 16.93 | 39.41 | 43.68 | 71.07 |

Formulations 1–7 in Table 7 demonstrate the differences in High Humidity Curl Retention that may be achieved through formulation of a successful hair fixative film.

We claim:
1. A hair fixative film comprising:
(a) at least one hair fixative polymer comprising a mixture of synthetic and natural polymers, wherein the ratio of synthetic to natural polymer is from about 20:80 to about 75:25 and wherein the synthetic polymers are selected from the group consisting of acrylates copolymer, polyurethane, polystyrenic, polyvinyl amide, polyvinyl ester, acrylates/octylacrylamide copolymer and mixtures thereof; and
(b) a plasticizer;
wherein the hair fixative film is an unsupported film and has a thickness of about 1 to about 500 microns,
wherein the hair fixative film provides hair stiffness of from about 0.004 Joules to about 0.030 Joules when applied to hair,
wherein the hair fixative film dissolves when exposed to water, and
wherein the hair fixative film has a high humidity curl retention of greater than 30 percent after 2 hours.

2. The film of claim 1, wherein said plasticizer is selected from the group consisting of polyol, polycarboxylic acid, dimethicone copolyol, polyester and mixtures thereof.

3. The film of claim 1, wherein said plasticizer is selected from the group consisting of propylene glycol, glycerol, dipropylene glycol, hydrolyzed wheat protein, hydrolyzed wheat starch, PEG-12 dimethicone and mixtures thereof.

4. The film of claim 1 wherein the synthetic polymer is selected from the group of octylacrylamide/acrylates/butylaminoethyl methacrylate, VA/crotonates/vinylneodecanoate copolymer, polyvinyl pyrrolidone, polyvinylpyrrolidone/vinylacetate copolymer and mixtures thereof, and the natural polymer is selected from the group consisting of xanthan gum, physically modified starch, chemically modified starch, polyquaternium-10, polyquaternium-4 and mixtures thereof.

5. The hair fixative film of claim 1 further comprising about 1 to 30 percent of a base based on total weight of the film.

6. The film of claim 5, wherein the fixative polymer is a mixture of octylacrylamide/acrylates/butylaminoethyl methacrylate, polyvinyl pyrrolidone, and modified corn starch, and wherein the ratio of synthetic polymer to natural polymer is in a range from about 35:65 to about 42:58, and wherein the plasticizer is propylene glycol in a range from about 8 to about 11 percent.

7. The film of claim 5, wherein the fixative polymer is a mixture of polyquaternium-4, corn starch modified, and polyvinylpyrrolidone/vinylacetate copolymer, and wherein the ratio of synthetic polymer to natural polymer is in a range from about 29:71 to about 33:67, and wherein the plasticizer is propylene glycol in an amount from about 6 to 9 percent.

8. A method of styling hair, comprising:
dissolving the hair fixative film of claim 1 in a solvent, and applying the hair fixative film to hair.

9. The film of claim 1 wherein the plasticizer is present in an amount of 5 to 30 percent by weight, based on total weight of the hair fixative film.

10. The film of claim 1 wherein the plasticizer is present in an amount of 5 to 15 percent by weight, based on total weight of the hair fixative film.

11. The film of claim 1 wherein when the at least one hair fixative polymer comprises at least 60% (wt/wt) of natural polymer based upon total weight of the hair fixative polymer, the plasticizer is present in an amount greater than 15 percent based upon weight of the natural polymer.

12. The film of claim 1 wherein the hair fixative film provides hair stiffness of from about 0.012 Joules to about 0.025 Joules when applied to hair.

13. The film of claim 1 further comprising at least one effervescing agent.

14. The film of claim 13 wherein the effervescing agent comprises an acid component and an alkaline component.

* * * * *